(12) United States Patent
Bouhnik et al.

(10) Patent No.: US 9,801,597 B2
(45) Date of Patent: Oct. 31, 2017

(54) MULTI-DETECTOR IMAGING SYSTEM WITH X-RAY DETECTION

(71) Applicant: General Electric Company, Schenectady, NY (US)

(72) Inventors: Jean-Paul Bouhnik, Zichron Yaacov (IL); Jiang Hsieh, Brookfield, WI (US); Riyad Mahameed, Umm al-Fahm (IL); Yaron Hefetz, Kibbutz Alonim (IL)

(73) Assignee: General Electric Company, Schenectady, NY (US)

( * ) Notice: Subject to any disclaimer, the term of this patent is extended or adjusted under 35 U.S.C. 154(b) by 684 days.

(21) Appl. No.: 14/494,973

(22) Filed: Sep. 24, 2014

(65) Prior Publication Data

US 2016/0081641 A1    Mar. 24, 2016

(51) Int. Cl.
| | | |
|---|---|---|
| *A61B 6/03* | (2006.01) | |
| *A61B 6/00* | (2006.01) | |
| *A61B 6/06* | (2006.01) | |
| *G06T 5/00* | (2006.01) | |
| *G06T 7/00* | (2017.01) | |
| *G06T 7/11* | (2017.01) | |

(52) U.S. Cl.
CPC ............ *A61B 6/4435* (2013.01); *A61B 6/032* (2013.01); *A61B 6/035* (2013.01); *A61B 6/037* (2013.01); *A61B 6/06* (2013.01); *A61B 6/4007* (2013.01); *A61B 6/4078* (2013.01); *A61B 6/4241* (2013.01); *A61B 6/4258* (2013.01); *A61B 6/4266* (2013.01); *A61B 6/4417* (2013.01); *A61B 6/5205* (2013.01); *G06T 5/002* (2013.01); *G06T 7/11* (2017.01); *G06T 7/97* (2017.01); *G06T 2207/10108* (2013.01); *G06T 2207/10116* (2013.01); *G06T 2207/30004* (2013.01); *G06T 2207/30196* (2013.01)

(58) Field of Classification Search
CPC ......... A61B 6/032; A61B 6/035; A61B 6/037; A61B 6/4241; A61B 6/4258; A61B 6/5229; A61B 6/5235; A61B 6/4417
See application file for complete search history.

(56) References Cited

U.S. PATENT DOCUMENTS

| | | |
|---|---|---|
| 5,338,936 A | 8/1994 | Gullberg et al. |
| 5,376,795 A | 12/1994 | Hasegawa et al. |
| 6,399,951 B1 | 6/2002 | Paulus et al. |
| 6,661,866 B1 | 12/2003 | Limkeman et al. |
| 6,956,925 B1 | 10/2005 | Hoffman |

(Continued)

OTHER PUBLICATIONS

International Search Report and Written Opinion from corresponding PCT application PCT/US2015/045097, dated Dec. 4, 2015; 11 pages.

*Primary Examiner* — Thomas R Artman
(74) *Attorney, Agent, or Firm* — Lucas Divine

(57) ABSTRACT

An imaging system is provided that includes a gantry having a bore extending therethrough; a plurality of image detectors attached to the gantry and radially spaced around a circumference of the bore such that gaps exist between image detectors along the circumference of the bore; an x-ray source attached to the gantry, wherein the x-ray source transmits x-rays across the bore towards at least two of the image detectors; wherein at least two image detectors detect both emission radiation and x-ray radiation.

26 Claims, 18 Drawing Sheets

(56) References Cited

U.S. PATENT DOCUMENTS

| | | | |
|---|---|---|---|
| 6,976,784 B2 * | 12/2005 | Kojima | G01T 1/1648 378/197 |
| 7,323,689 B2 | 1/2008 | Hawman | |
| 7,374,337 B2 | 5/2008 | Yunker | |
| 8,139,713 B2 | 3/2012 | Janbakhsh | |
| 2007/0025522 A1 | 2/2007 | Fenster et al. | |
| 2011/0103544 A1 | 5/2011 | Hermony | |
| 2012/0085912 A1 | 4/2012 | McCroskey et al. | |
| 2014/0270056 A1 * | 9/2014 | Zou | A61B 6/4266 378/19 |
| 2016/0081635 A1 * | 3/2016 | Divine | A61B 6/06 378/19 |
| 2016/0081641 A1 * | 3/2016 | Bouhnik | G06T 7/97 378/5 |

\* cited by examiner

MULTI-DETECTOR IMAGING SYSTEM WITH X-RAY DETECTION

BACKGROUND

The subject matter disclosed herein relates generally to medical imaging systems, and more particularly to diagnostic imaging systems which combines Computed Tomography (CT) with a Nuclear Medicine (NM) Single Photon Emission Computed Tomography (SPECT) system.

In CT imaging, a patient is placed in a gantry. The gantry can comprise a stationary frame for supporting a rotary member. The rotary member includes a central opening, or bore, large enough to receive a patient extending along the scanning axis. The rotary member is rotated about a patient during a scanning or imaging procedure. An x-ray tube can be positioned on the rotary member diametrically across the central opening from an array of x-ray detectors. As the rotary member rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

In NM imaging, such as SPECT or PET imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

In a NM system, it can be advantageous to collect CT information for purposes of attenuation correction, body shape planning, scouting specific organs, and other known benefits of CT data. It is needed to provide such a system that is low-cost and efficient.

BRIEF DESCRIPTION

In accordance with an embodiment, an imaging system is provided that includes a gantry having a bore extending therethrough; a plurality of image detectors attached to the gantry and radially spaced around a circumference of the bore such that gaps exist between image detectors along the circumference of the bore; an x-ray source attached to the gantry, wherein the x-ray source transmits x-rays across the bore towards at least two of the image detectors; wherein one or more detectors detect both emission radiation and x-ray radiation.

The system can further include a stationary structure and a rotary member; wherein the x-ray source is attached to the rotary member and the plurality of image detectors are attached to the stationary structure; and wherein the rotary member rotates to allow the x-ray source to orbit an imaging subject inside the bore, each image detector further comprising a sweep motor; a detector head comprising detector elements; and wherein, if the image detector is in an x-ray transmission fan beam, the sweep motor adjusts the angle of the detector head to be directed at the x-ray source. The image detectors can further comprise a radial motor for extending the image detector closer to and retracting the image further from a region of interest; and wherein, if the image detector is not in the x-ray transmission fan beam, the sweep motor adjusts an angle of the detector head to be directed at the region of interest and the radial motion motor extends or retracts the image detector based on its distance to the region of interest.

In an alternative embodiment, the plurality of image detectors are attached to the rotary member and the x-ray source is attached to the stationary structure; and wherein the rotary member rotates to allow the imaging detectors to orbit an imaging subject inside the bore. Alternatively, the gantry can include two rotary members wherein both rotary members are annular; and wherein the plurality of image detectors are attached to the first rotary member and the x-ray source is attached to the second rotary member. In this case the plurality of detectors could rotate around the bore on an outer circumference; and the x-ray source could rotate around the bore on an inner circumference.

The gaps in the system may receive radiation such that the transmitted x-rays are transmitted in a fan beam; and more than fifty percent of the fan beam angle is gap transmission in that x-rays enter the gaps and do not hit an image detector. In this case the system could further comprise a source collimator; and wherein a processor in the system directs the collimator to block gap transmissions. The image detectors can be regularly spaced around the circumference of the bore such that the gaps between image detectors are substantially equivalent. Alternatively the image detectors can be irregularly spaced around the circumference of the bore such that the gaps between image detectors are not equivalent.

The system contains an image reconstruction module that: receives emission radiation and x-ray radiation from the plurality of image detectors and generates medical images; and outputs the medical images to a display or a memory device. The image reconstruction module can use the emission radiation to reconstruct a first medical image and uses the x-ray radiation to perform attenuation correction on the first medical image to generate a second medical image. If image detectors further comprise a sweep motor; a detector head comprising detector elements; and a radial motor for extending and retracting the image detector; then the image reconstruction module can use the x-ray radiation to determine the location of a region of interest; the radial motor extends the image detector towards the region of interest; the sweep motor adjusts the detector head angle to be directed towards the region of interest; and the detector elements detect emission radiation. Further, the image reconstruction module can use the emission radiation to reconstruct a second medical image and uses the x-ray radiation to determine an anatomical shape related to the second medical image.

Additional features of the system can include the configurations that the x-ray source transmits low-power x-rays, the image detectors further comprise detector elements made from Cadmium Zinc Telluride (CZT), the system has a second x-ray source attached to the gantry, the x-ray source and the plurality of image detectors share an X-Y plane, the image detectors are photon counting detectors, or the emission radiation is single photon emission computed tomography (SPECT) radiation.

In an embodiment, the system can activate the image detectors that are in an x-ray transmission fan beam and does not activate the image detectors that are outside of the x-ray transmission fan beam.

In an embodiment, a gantry is provided including a bore extending therethrough; a rotary member; an x-ray source attached to the rotary member, wherein the rotary member rotates the x-ray source around the circumference of the bore; a plurality of image detectors attached to the gantry and radially spaced around a circumference of the bore such that gaps exist between image detectors along the circumference of the bore; each image detector further comprising a detector head and a sweep motor to adjust the angle of the detector head; wherein at least two sweep motors adjust the angle of the respective detector head towards the x-ray source; and wherein the image detectors detect x-ray radiation.

In an embodiment, an imaging method is provided including rotating an x-ray source around the circumference of a gantry bore; receiving transmitted x-ray radiation at a plurality of image detectors spaced evenly around the circumference of the bore such that gaps exist between image detectors along the circumference of the bore; receiving emission radiation at a plurality the plurality of image detectors; generating a medical image based on the emission radiation and x-ray radiation. The method can include that the emission data is used to generate an intermediate image; and the x-ray data is used to perform attenuation correction on the intermediate image to generate the medical image. The method can also include determining a region of interested based on the x-ray radiation; and adjusting the angle of at least two detector heads to be directed towards the region of interest.

DETAILED DESCRIPTION

Figure 1:
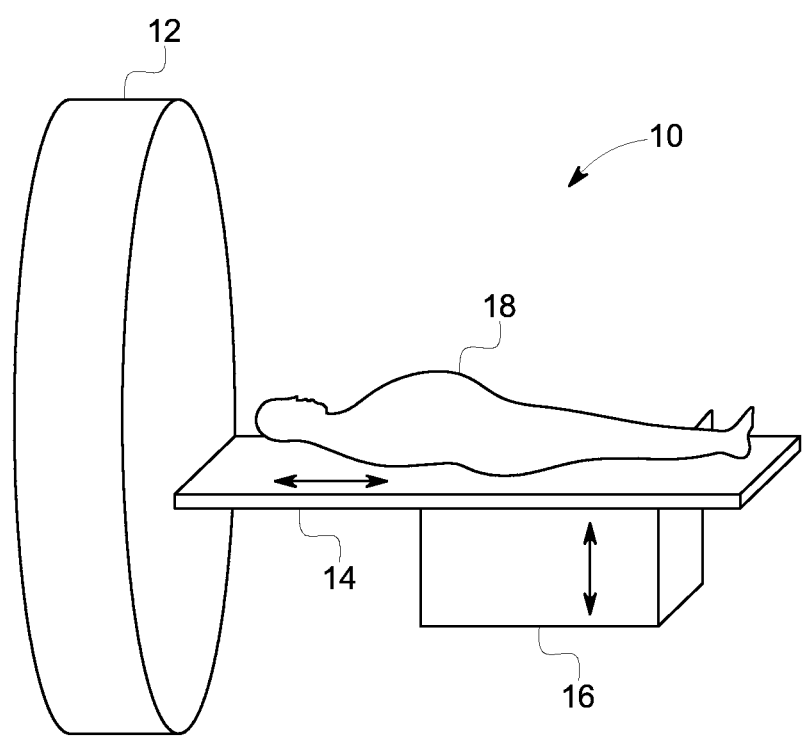
FIG. 1 shows a medical imaging system, according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with imaging detectors mounted thereto. For example, in various embodiments of an NM imaging system, a Single Photon Emission Computed Tomography (SPECT) imaging scanner is provided that includes a plurality of detectors with a combination of different types of detectors that acquire SPECT and CT image information. This can be done at different time intervals or simultaneously. The various embodiments may include detectors formed from different materials, having different configurations or arrangements, and/or having different collimation. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system.

FIG. 1 shows medical imaging system 10, according to an embodiment. Subject 18 can be a human patient in one embodiment. Alternatively, subject 18 is not human. It can be some other living creature or inanimate object in various embodiments. Subject 18 can be placed on a pallet 14 that can move a subject horizontally for locating subject 18 in the most advantageous imaging position. The bed mechanism 16 can raise and lower pallet 14 vertically for positioning subject 18 in the most advantageous imaging location. Gantry 12 is shown as circular in an embodiment. In other embodiments gantry 12 may be of any shape such as square, oval, "C" shape, or hexagonal. Gantry 12 has a bore for subject 18 to enter therein.

Figure 2:
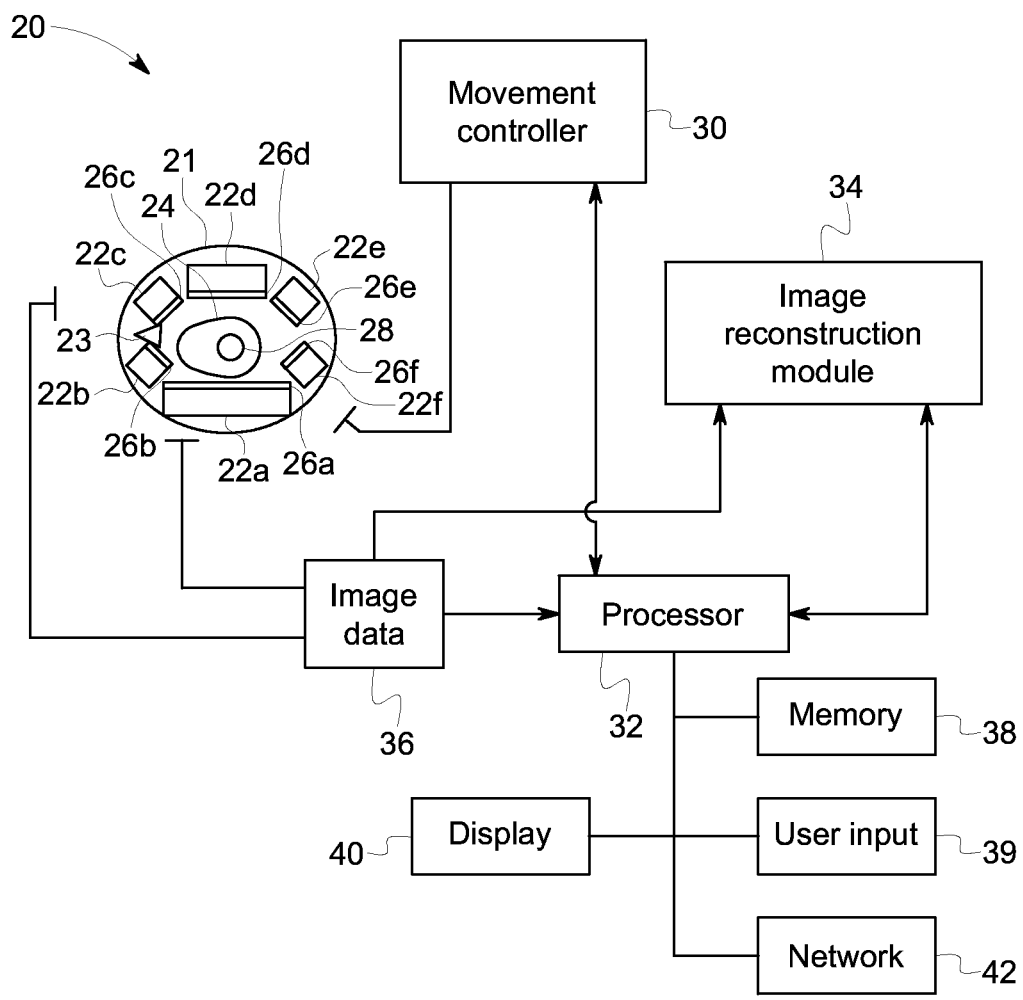
FIG. 2 shows a block diagram of a medical imaging system, according to an embodiment.

FIG. 2 shows a block chart of medical imaging system 20, according to an embodiment. A portion of patient 24 is positioned inside the bore of gantry 21. The medical imaging system 20 may be provided having a plurality of radiographic cameras configured as dual CT/SPECT detector columns 22a-22f. Detector columns 22 are attached to gantry 21, either to a stationary section of gantry 21 or its rotary member. It should be noted that the various embodiments are not limited to the medical imaging system 20 having six detector columns 22 as shown or to the sizes or shapes of the illustrated detector columns 22. For example, the medical imaging system 20 may include more or less detector columns 22 having different shapes and/or sizes, or formed from different materials. Detector columns can be called detector units in some embodiments. X-ray source (e.g. an x-ray tube) 23 is also attached to gantry 21, either to a stationary section or the gantry's rotary member. X-ray source can transmit both low-power and high-power x-ray's towards patient 24. X-ray source can transmit both low-flux and high-flux x-ray's towards patient 24.

In operation, a subject, such as patient 24, is positioned in proximity to the one or more of detector columns 22 for imaging. The imaging system 20 can then re-adjust the detector columns 22 to retract further from or extend closer to patient 24 or patient region of interest (ROI) 28 as needed, which is a heart in an example embodiment. Imaging of patient 24 is performed by one or more of detector columns 22. The imaging is performed based on x-ray transmission data, originating from x-ray source 23, and based on emission data caused by a radiopharmaceutical tracer inside patient 24. The imaging by each of the detector columns 22 may be performed simultaneously, concurrently, or sequentially.

The position of the detector columns 22 may be varied, including the relative position between detector columns 22, the tilt, the angle, the swivel, and other characteristics of the detector columns 22. Additionally, each of the detector columns 22 may have a corresponding collimator 26a-26f mounted or coupled thereto. The collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, the detector column 22 wholly includes collimator 26.

The detector columns 22 may include single crystal, or multi-crystal, detectors or pixelated detectors or scintillator based detectors that are configured to acquire SPECT and CT image data. These may be referred to as detector elements. For example, the detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum (III) bromide ($LaBr_3$), among others. Additionally suitable components may be provided. For example, the detector columns 22 may be coupled to photosensors, such as an array of Photo-Multiplier Tubes (PMTs), an Avalanche Photodiode Detector (AFD), etc. Additionally, PET image data can be acquired in some embodiments. The detector elements are photon counting detectors in some embodiments. The detector elements are direct conversion or solid state in some embodiments.

Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV) while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

Imaging system 20 can also include a movement controller 30 that operates to control the movement of the x-ray source 23, detector columns 22 and/or other moving parts in gantry 21, such as its rotary member. For example, the movement controller 30 may control movement of the detector columns 22, such as to rotate or orbit the detector columns 22 around a patient 24, and which may also include moving the detectors closer to or further from the patient 24 and pivoting/swiveling the detector columns 22, such that localized movements or motions are provided. Detector controller 30 additionally may control the orbital rotation of detector columns 22 around the edges of the gantry bore, such that detector columns 22 are at a new angle to patient 24 than previously. In various embodiments, the movement controller 30 may be a single unit or multiple units controlling each separate apparatus.

The imaging system 20 also includes image reconstruction module 34 configured to generate images from acquired image data 36 received from the detector columns 22. For example, image reconstruction module 34 may operate using NM image reconstruction techniques to generate SPECT images of the patient 24, which may include an ROI 28, such as the heart of a patient. The image reconstruction techniques may be determined based on the installation status of detector column 22 acquiring the image data 36 and sending to image reconstruction module 34 and/or processor 32.

Image reconstruction module 34 may be implemented in connection with movement controller 30 and/or processor 32. Optionally, the image reconstruction module 34 may be implemented as a module or device that is coupled to or installed in the movement controller 30 and/or processor 32. Each processing module may be a separate hardware module or software module, or combined together into one chip or module in various embodiments.

CT and/or SPECT image data 36 is received by the processor 32 and/or image reconstruction module 34 may be stored for a short term (e.g., during processing) or for a long term (e.g., for later offline retrieval) in a memory 38. The memory 38 may be any type of data storage device, which may also store databases of information. Memory 38 may be separate from or form part of the processor 32. User input 39, which may include a user interface selection device, such as a computer mouse, voice activation, trackball and/or keyboard is also provided to receive a user input. User input 39 may direct processor 32 to send a movement control signal to movement controller 30 for alteration of detector column 22 and/or x-ray source 23 arrangements in the gantry. Optionally, user input 39 may be considered by the processor 32 as a suggestion and the processor 32 may choose to not execute the suggestion based on criteria.

Thus, during operation, the output from the detector columns 22, which may include image data 36, such as projection data from a plurality of detector/gantry angles is transmitted to processor 32 and image reconstruction module 34 for reconstruction and formation of one or more images. The reconstructed images and other user output can be transmitted to a display 40 such as a computer monitor or printer output. The reconstructed images and other user output can also be transmitted to a remote computing device via network 42.

Figure 3:
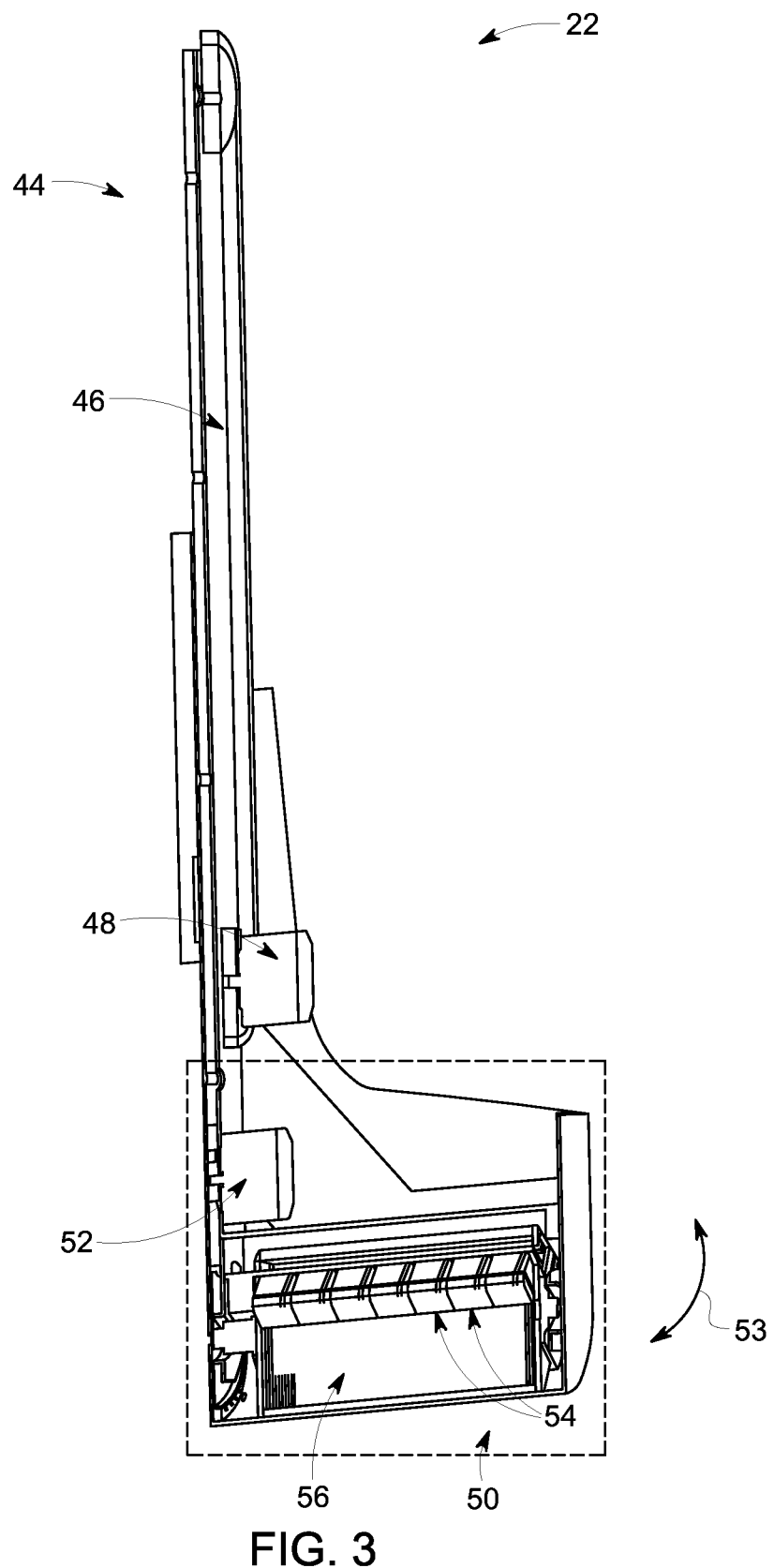
FIG. 3 shows an implementation of a detector column, according to an embodiment.

FIG. 3 shows an implementation of detector column 22, according to an embodiment. Column arm 44 attaches to a gantry and provides support for and includes a radial motion rail 46, radial motion motor 48, and detector head 50. Radial motion motor 48 controls the movement of detector head 50 by extending or retracting detector head 50 along radial motion rail 46. This provides customizability and flexibility to the imaging system. The detector column can include telescopic covers that allow it to extend and contract as it moves radially in and out.

The detector head 50 includes sweep motor 52, detector elements 54, and collimator 56. Detector elements 54 can be CZT modules or other detector element modules for detecting CT and SPECT image data. Sweep motor 52 controls the rotation angle of the detector head 50 in relation to the arm 44. Sweep pivoting axis 53 shows the rotation angle axis of the detector head 50. Movement controller 30 can provide instruction and control to either or both of the radial motion motor 48 and sweep motor 52. Thus, each detector column 22 is independently controllable in the radial location as well as the angle of tilt of the detector head 50. Radial motion motor 48 and sweep motor 52 can be two separate motors as shown in the embodiment of FIG. 3. Alternatively, the functionality of the two motors may be provided by one motor.

Figure 4:
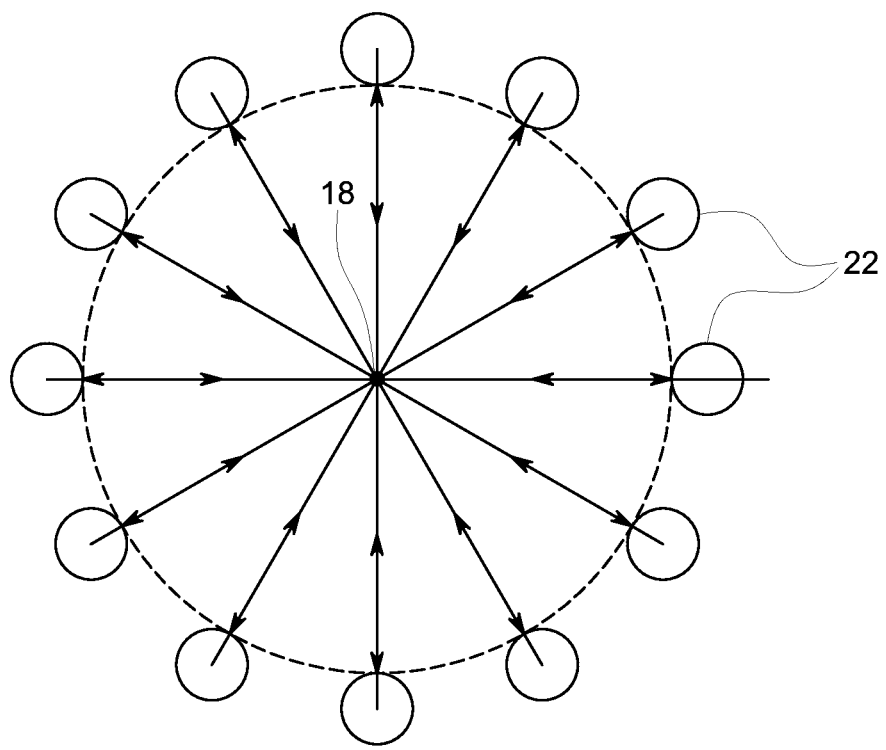
FIG. 4 shows a radial construction of an imaging system, according to an embodiment.

FIG. 4 shows a radial construction of an imaging system where twelve detector columns 22 are placed at a consistent angle, thirty degrees in this example, from each other along the circumference of a gantry bore, according to an embodiment. FIG. 4 also shows physical gaps between detector columns 22. Thus, the detector columns 22 are uniformly distributed in this example. Each detector column 22 is movable along a radial axis. This allows the detector heads on detector columns 22 to be closer or further from a subject 18 for imaging. The gap between two detector heads decreases as the detector columns are extended towards the center of the bore. The circles in the figure depict the location of detector head 50 of detector column 22. The detector columns are shown along the dotted line as their outer limit position in this view of one embodiment. The dual head radial arrows depict the in-out direction of motion of the detector columns 22.

Figure 5:
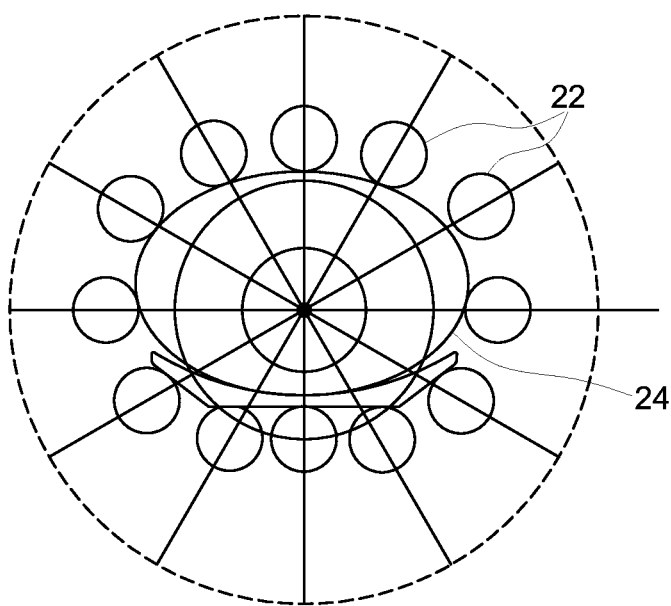
FIG. 5 shows a radial construction of an imaging system where twelve detector columns have their heads placed at a consistent angle and have been moved radially inward to be in positions close to a patient, according to an embodiment.

FIG. 5 shows a radial construction where twelve detector columns 22 have their heads placed at a consistent angle and have been moved radially inward to be in positions close to a patient 24, according to an embodiment. As FIG. 5 shows, some of the detector heads are further towards the center of their radial axis than others. This allows for high-quality imaging results with varied-sized objects. The resolution of SPECT detection can degrade as an image detector moves further from the emission source.

Figure 6:
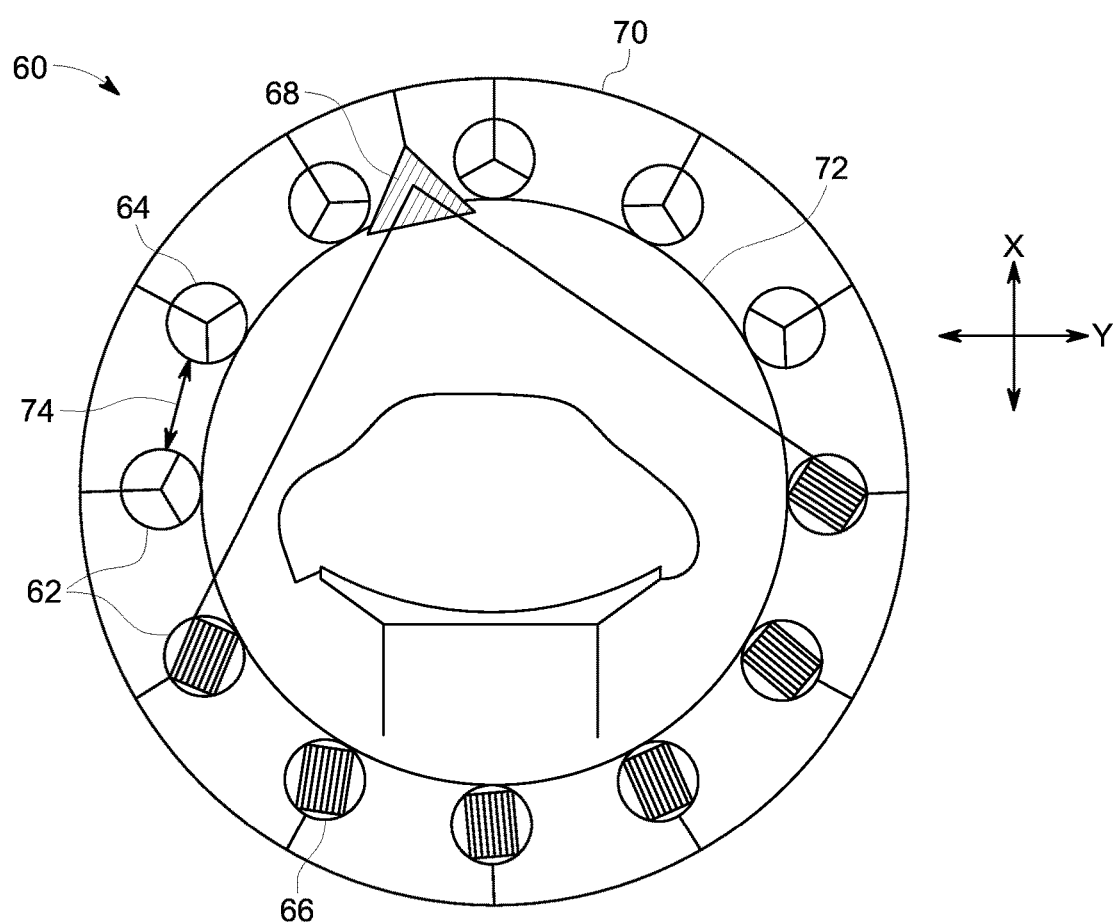
FIG. 6 shows a gantry in a medical imaging system, according to an embodiment.

FIG. 6 shows gantry 60 in a medical imaging system, according to an embodiment. Attached to gantry 60 are detector columns 62 radially spaced around a circumference of the bore, which can include active columns 66 and inactive columns 64. A space 74 exists between detector columns such that there is a gap in image detection coverage. X-ray tube 68 is also attached to gantry 60. X-ray tube 68 transmits x-ray radiation across the X-Y, or scanning, plane. FIG. 6 shows the x-ray transmission in a fan beam, according to an embodiment. Only active columns 66 that are within the fan beam are activated for image detection in one embodiment. Active columns 66 are columns currently in use to detect x-ray radiation transmitted from x-ray tube 68. Inactive columns 64 are not currently in use to detect x-ray radiation. Emission detection from an in-patient tracer can be detected from active column or an inactive column, as active and inactive in this context refer to x-ray radiation detection.

FIG. 6 also shows the detector heads of active columns 66 angled to be pointing towards x-ray tube 68 to achieve the best image quality. Active columns 66 can point towards the x-ray tube focal spot in an embodiment. Sweep motor 52 angles the detector heads towards x-ray tube 68 if the detector column 62 is in the active zone of the x-ray transmission and can return the detector head angle to a standard position or angled at an emission ROI if the detector column 62 is not in the active zone of the x-ray transmission.

Detector columns 62 may be attached to the gantry via a rotary member 70 or a stationary structure. Detector columns 62 may be regularly spaced around the circumference of the bore as shown by example in FIG. 6 or irregularly spaced around the circumference of the bore as shown by example in FIG. 2. X-ray tube 68 may be attached to the gantry via a rotary member 70 or a stationary structure. In some embodiments both detector columns 62 and x-ray tube 68 are attached to the gantry via a rotary member 70. Rotary member 70 is annular in an embodiment. Annular member 72 can be part of rotary member 70 in one embodiment. Annular member 72 can be a second rotary member as discussed further below with regard to FIG. 7.

Figure 7:
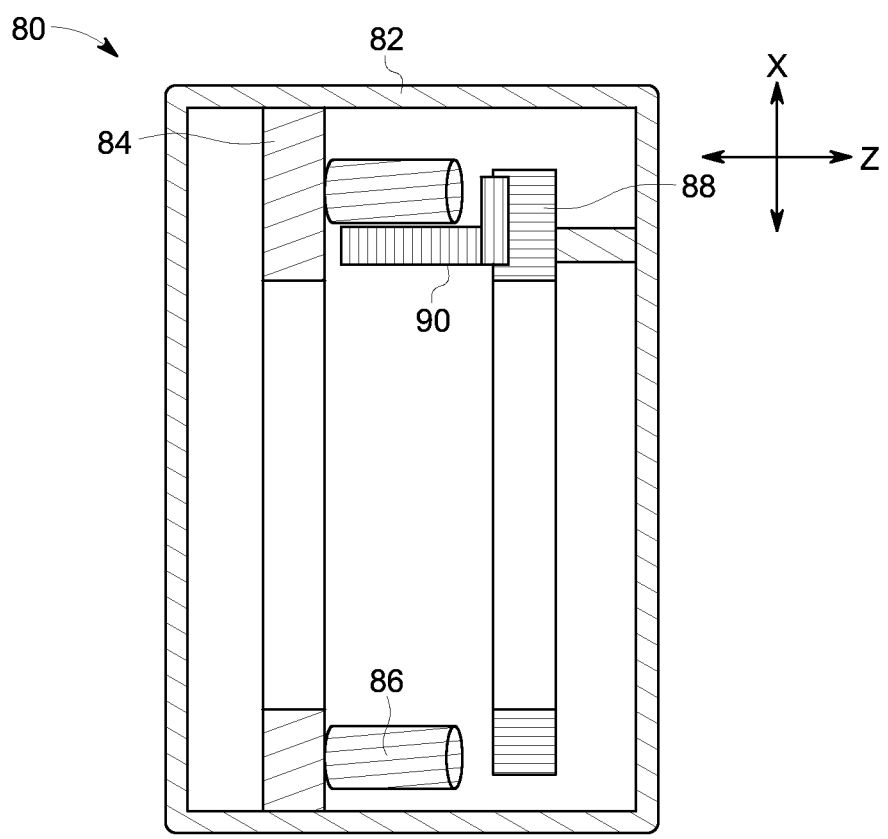
FIG. 7 shows a side view of a gantry in an imaging system, according to an embodiment.

FIG. 7 shows a side view of gantry 80 in an imaging system, according to an embodiment. A patient can be positioned into the gantry bore along the z-axis for medical imaging as shown in FIG. 1. Stationary structure 82 provides a housing and support for the system. First rotary member 84 is attached to stationary structure 82 with detector columns 86 attached to it. Second rotary member 88 is attached to stationary structure 82 with x-ray tube 90 attached to it. FIG. 7 shows that x-ray tube 90 can rotate in an orbit around the center of the bore along an inner circumference, while detector columns 86 can orbit around the center of the bore along an outer circumference. This prevents any collision of elements and any occlusion of the x-ray transmission by detector columns on the same side of the bore. In alternative embodiments, one of the two rotary members can be stationary, fixed to the gantry. In an alternative embodiment, the x-ray tube is attached to the same rotary member as the detector columns, discussed further below.

In an embodiment, x-ray tube 90 is moved in the Z-direction out of the X-Y plane of the imaging detectors when not in use. This allows for full extension and retraction of detector columns 86 during an NM imaging phase. In an alternate embodiment, x-ray tube 90 can be rotated orbitally by second rotary member 88 to a position that is between two detector columns 86, also allowing full extension and retraction of detector columns 86 during an NM imaging phase.

Figure 8:
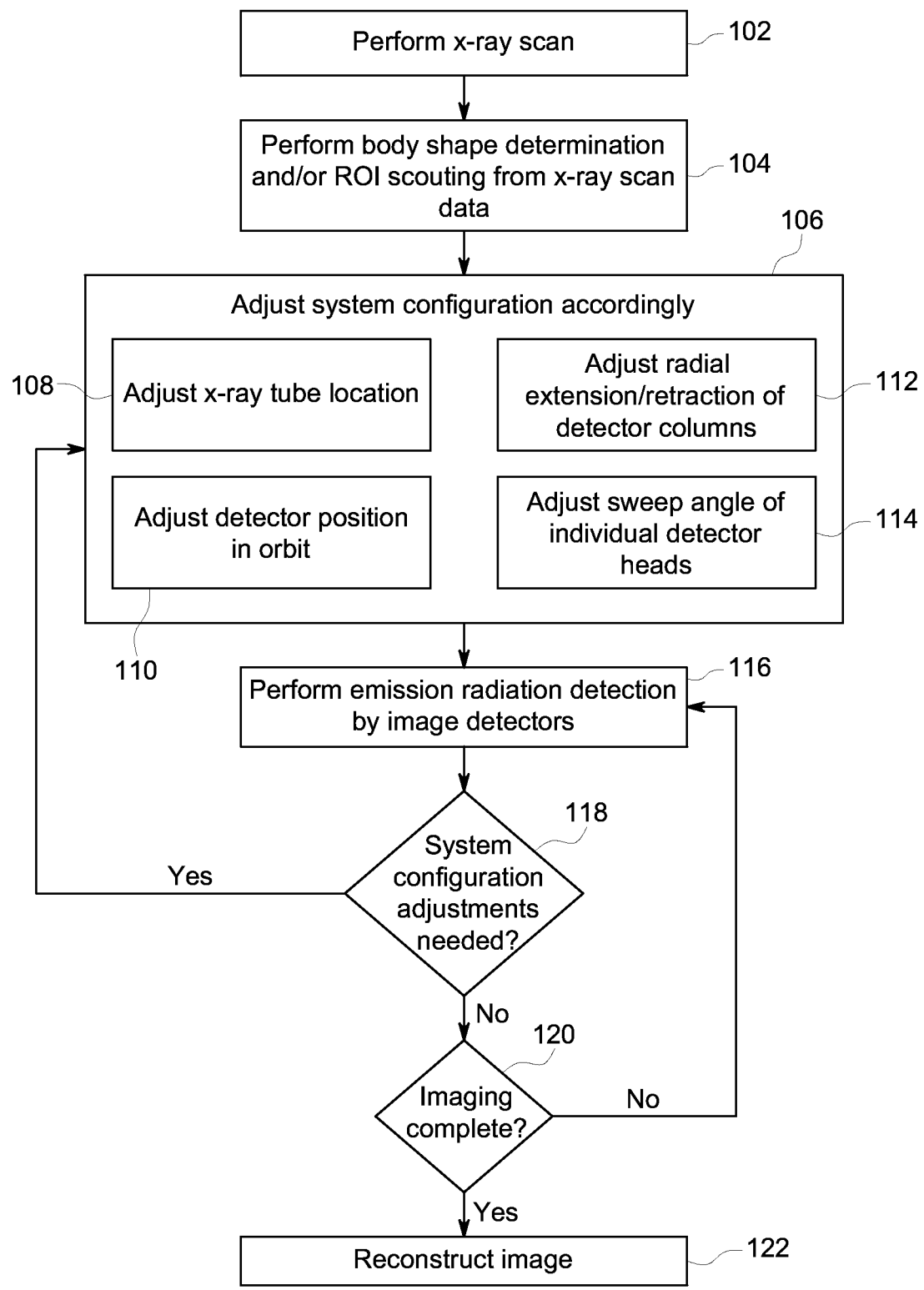
FIG. 8 shows the steps of an imaging operation using both x-ray and emission data, according to an embodiment.

FIG. 8 shows the steps of an imaging operation detecting both x-ray and emission data, according to an embodiment. The imaging system can use x-ray data to derive CT information to assist in body shape determination and/or ROI scouting. This allows the NM imaging operation to be performed with higher accuracy and performance by allowing the detector columns to focus on the correct aspects of the patient. The detector columns thus have helpful information to extend or retract at appropriate times. The sweep motors can determine what angles the detector heads should be positioned. And the rotary member supporting the detector columns has information on when it should rotate for maximum imaging. This process may be called planned focused acquisition. It includes the ability to plan the positioning and motion of the detectors to focus the attention of the detector on the target zones. This can save acquisition time, reduces risk of patient movement, increase patient comfort, and the useful output of the image detector.

In step 102, the system performs an x-ray scan, which is discussed further throughout. In step 104, the x-ray scan data is converted to CT data for determining body shape information and/or region of interest scouting. Body outer shape determination helps the system plan the NM imaging acquisition and helps avoid collisions of the detector heads with the body in such system with extendable and retractable detector columns. Scouting the organs of interest to be imaged in the body helps the system focus on the correct locations for best image quality of the organ. The system can also thus detect which detector columns (if the detector columns are not all the same) may be best for the specific scan. This can be in a situation where some detector columns have higher quality materials or materials specifically tailored to the needs of the scan to be performed. The scan to be performed can depend on the type of scan and scan protocol selected by a user or the system based on some criteria. The selections can be communicated across a computer network to the imaging system.

In step 106, the imaging system, through electronics, processor, and computer code, adjusts the system configuration according to the information developed in step 104 or step 118. The adjustments can include, but are not limited to, the actions in steps 108-114. In step 108, the system adjusts the x-ray tube location, either radially around the circumference of the bore, or in the Z-direction. This can be to continue an x-ray acquisition or to position the x-ray tube in a standby location. In step 110, the system adjusts the orbital location of one or more detector columns radially around the circumference of the bore. In step 112, the system extends or retracts one or more independently movable detector columns. In step 114, the system adjusts the sweep angle of one or more of the independently controllable detector heads by use of the sweep motors. These steps are generally done to improve NM or CT imaging. While not shown in FIG. 8, the system may also adjust the position of the table supporting the patient in step 106, in the X, Y, and/or Z directions.

In step 116, the system performs NM imaging by detecting emission data from within a subject or patient. Some or all of the detector columns may be activated for step 116. In step 118, the system determines if hardware configuration adjustments are needed, as done by step 106. If YES, the system returns to step 106 for one or more system reconfiguration actions to be completed. If NO, the system moves to step 120. In step 120, the system determines if the imaging operation is complete. If NO, additional data is collected at step 116. If YES, the system moves to step 122. In step 122, the system reconstructs the image. The reconstruction can be done from just the emission data, or the emission and x-ray data in conjunction. This reconstruction can be done through iterative reconstruction or other techniques known in the art of medical imaging. The reconstructed image is then stored in a computer memory and/or displayed on a screen to a user, according to an embodiment.

Figure 9:
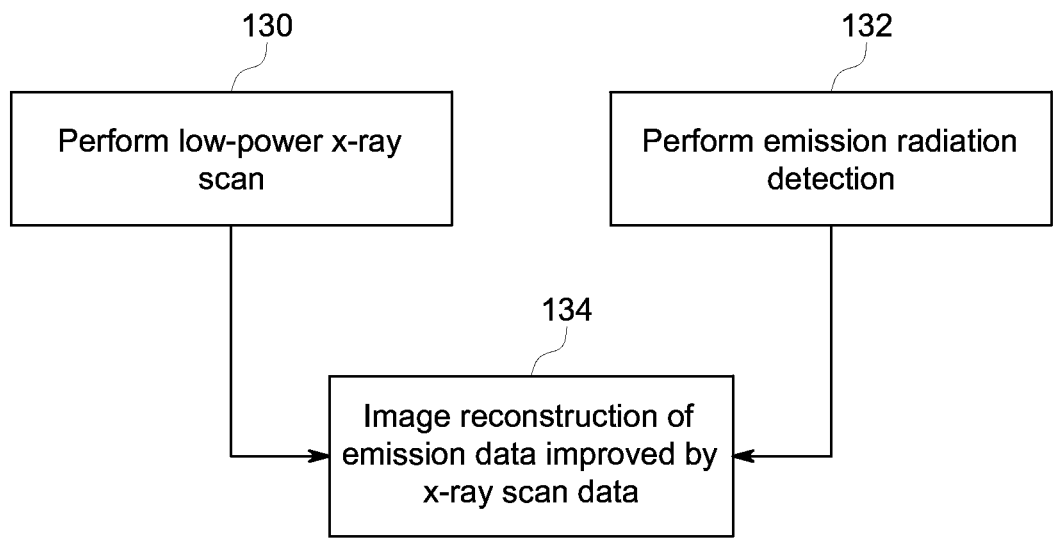
FIG. 9 shows the steps of a concurrent imaging operation, according to an embodiment.

FIG. 9 shows the steps of a concurrent imaging operation, according to an embodiment. In step 130, the system performs an x-ray scan by instructing the x-ray tube to transmit x-rays through the gantry bore towards one or more detector columns. As discussed further herein, the active detector columns in the fan beam of the x-ray transmission can angle their detector heads to point towards the x-ray tube. The x-ray scan can be low power or flux according to one embodiment. This allows certain materials, such as some CZT configurations, to be used for simultaneous acquisition of both x-ray and gamma ray (emission) data. Low power x-ray transmissions are generally below one kilowatt, according to one embodiment. Low power x-ray transmissions can be as low as one to twenty-five watts, according to one embodiment. In other configurations, the system may best perform with high power or flux x-ray transmissions. High power may be over ten or twenty kilowatts, according to one embodiment.

In step 132, simultaneous emission radiation detection occurs. Step 130 or 132 may be longer than the other, but simultaneous here means that they occur in overlapping time periods. The detector columns are dual use, according to an embodiment. As shown in FIG. 6, inactive columns 64 can be in a NM detection only mode. If x-ray tube 68 moves around the circumference of the gantry such that the fan beam includes an inactive column 64, the system can change the column into an active column 66, which can operate in a dual acquisition mode. In such a dual acquisition mode, the detector column can acquire both x-ray and emission information and separate the two with photon counting modes, energy windowing for tissue type discrimination, or other techniques known in the art. Emission data can be subtracted and filtered by energy values, according to an embodiment.

In step 134, an image reconstruction is done of the emission data acquired in step 132. The image reconstruction is improved by incorporating some of the results from the x-ray scan data from 130. Such improvements can be attenuation correction, localization of NM findings in relation to body organs, and cross registration to the diagnostic anatomical image from the x-ray data. As a consequence of attenuation, quantitative image values in the various projections do not accurately represent line integrals of the radioisotope distribution within the body. It is therefore necessary to correct for this distortion. If the emission data is to be corrected for attenuation, x-ray transmission data must be acquired at each station. Thus, attenuation correction provides a computer map of the density of the patient to correct the emission data. The attenuation computer map and emission data can be used for creation of an attenuation corrected isotope distribution image, without ever creating a non-corrected image, according to an embodiment.

The steps of FIG. 9 may include the system configuration adjustments of step 106, according to an embodiment.

Figure 10:
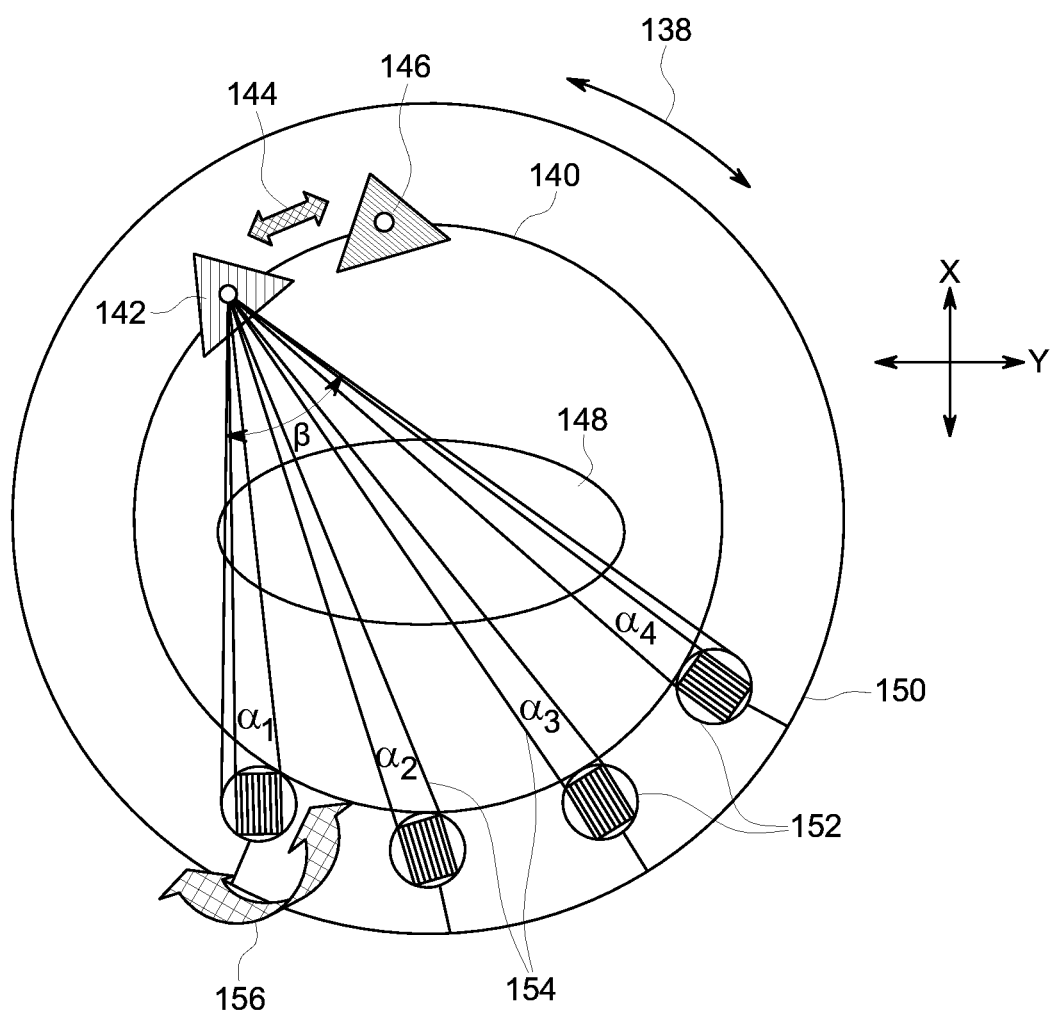
FIG. 10 shows a cross section of a gantry during an image scan, according to an embodiment.

FIG. 10 shows a cross section of a gantry during an image scan, according to an embodiment. Rotary member 140 is attached to a gantry and orbits along the outside of the bore, as indicated by arrow 138, along an inner circumference. Rotary member 140 is annular in an embodiment. X-ray tube 142 is attached to rotary member 140. X-ray arrow 144 shows the movement of the x-ray tube as the rotary member rotates. X-ray tube position 146 shows the position of the x-ray tube 142 after it has been rotated around the bore a certain distance.

X-ray tube 142 transmits x-rays that pass through subject 148 towards image detectors 152. Image detectors 152 are attached to stationary structure 150. Thus, in this embodiment, only one rotary member is included in the imaging system. This can save money compared to a two rotary member embodiment. Image detectors 152 can adjust their sweep motion 156 so they are pointing towards x-ray tube 142 as it moves to different positions, such as x-ray tube position 146, around the circumference of the bore. Thus, image detectors 152 capture the highest intensity x-rays.

The x-ray tube transmission can be in a fan beam configuration as shown in FIG. 10. The fan beam has an angle β, which can be around 80 degrees in an embodiment. It can change based on the specific x-ray tube installed and the specific settings in the hardware and software. The angular amount of the fan beam that hits each detector is window 154 defined by angle α. As shown in FIG. 10, the four detectors have four windows: α1, α2, α3, and α4. The total angle of coverage α1+α2+α3+α4 is less than the total angle β of the fan beam. This defines gaps that exist between image detectors 152. The gaps shown in FIG. 10 are over fifty percent of β, according to an embodiment. In alternate embodiments the gaps may be over eighty percent or as low as ten percent. This can change based on image detector size, amount of image detectors in the system, fan beam angle, and other factors. The system must work to overcome these gaps in coverage to acquire quality x-ray image data.

In an embodiment, x-ray tube 142 can include a collimator with the ability to block x-ray transmission to areas outside of α coverage, thus reducing radiation dose to subject 148. The system can perform a method to detect the current location of the x-ray tube around the circumference of the bore. The system can then detect image detector location and angles and compare them with the tube location. The system can then activate image detectors within the beam and calculate the gap angles (inside the beam but not hitting a detector. Then the system can instruct an adaptive collimator to block transmission to the gap angles. If the relative positioning between the source and detectors is fixed, then a fixed collimator may be used that blocks gap radiation.

FIGS. 11-14 show an x-ray data scan with gaps between image detectors, according to an embodiment. These image detectors can be detector columns with sweeping detector heads as discussed above.

Figure 11:
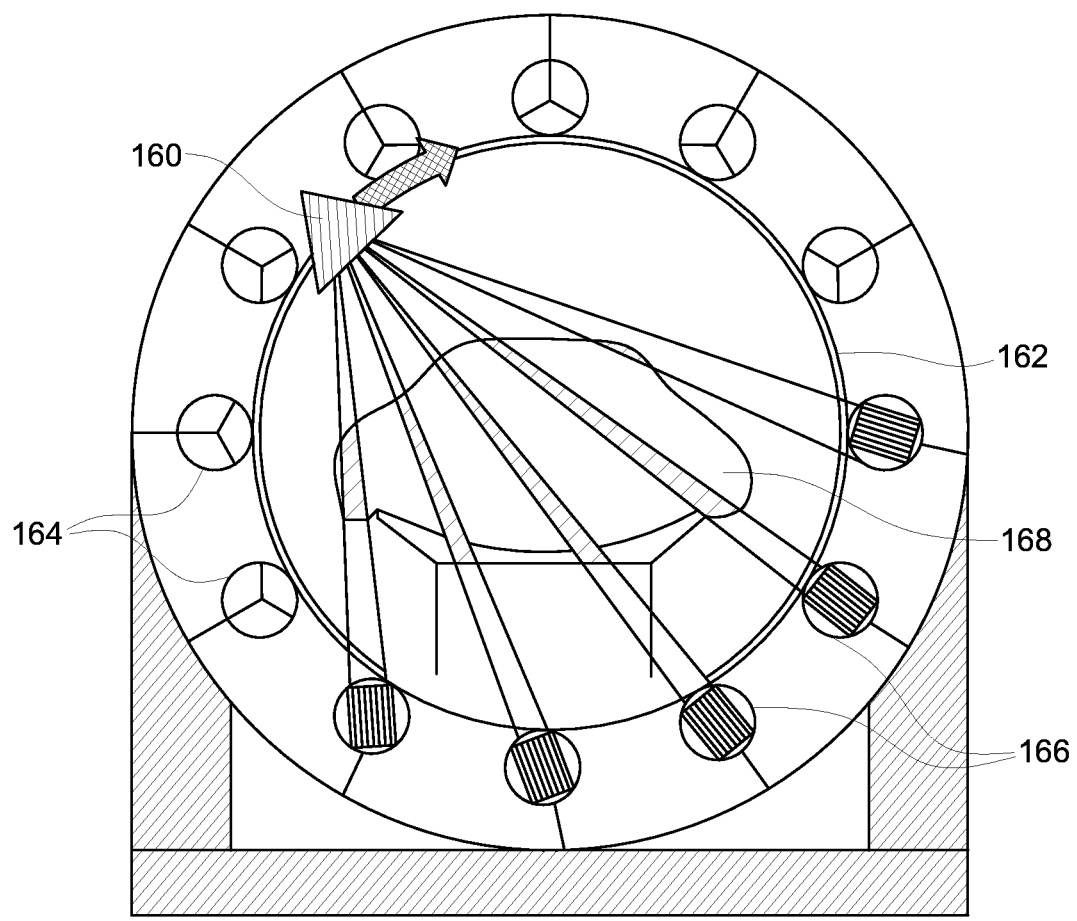
FIG. 11 shows the initial movement of an x-ray tube moving as attached to a rotating rotary member around a subject in the bore of a gantry, according to an embodiment.

FIG. 11 shows the initial movement of x-ray tube 160 moving as attached to rotating rotary member 162 around subject 168 in the bore of a gantry, according to an embodiment. Image detectors are attached around the outside of the gantry, in fixed location attached to a stationary structure of the gantry in an embodiment. Active detectors 166 are in use for the x-ray data acquisition. Inactive detectors 164 are not in use for the x-ray data acquisition. The system may also completely shut off certain detectors as the x-ray tube passes in front, occluding photon detection. This would be a blocked detector according to an embodiment. FIG. 11 shows five angles α of transmission to five active detectors 166. FIG. 11 shows the section of subject 168 that has been scanned. To address the gaps between detectors, rotary member 162 continues its orbit.

Figure 12:
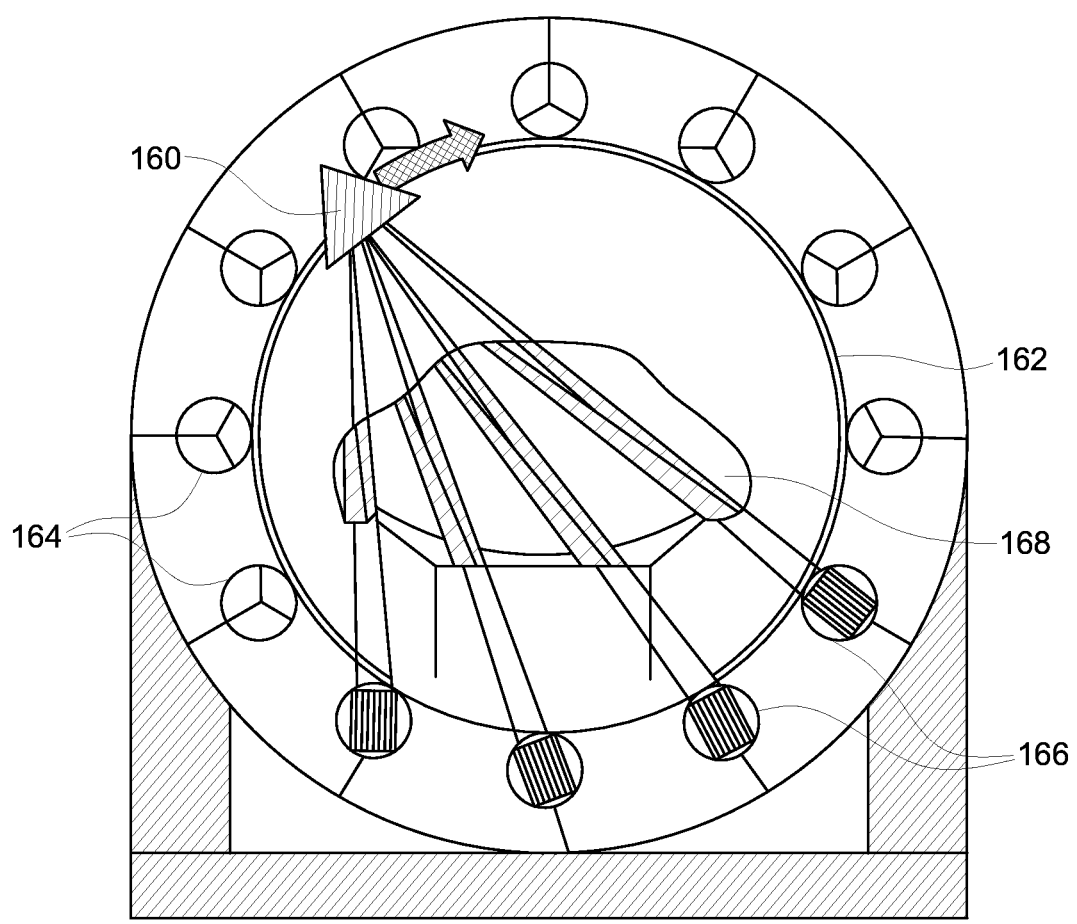
FIG. 12 shows a second movement location of an x-ray tube during an x-ray data scan, according to an embodiment.

FIG. 12 shows a second movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 12 shows only four angles α of transmission to four active detectors 166. The right-most detector, an active detector in FIG. 11, has become an inactive detector 164.

Figure 13:
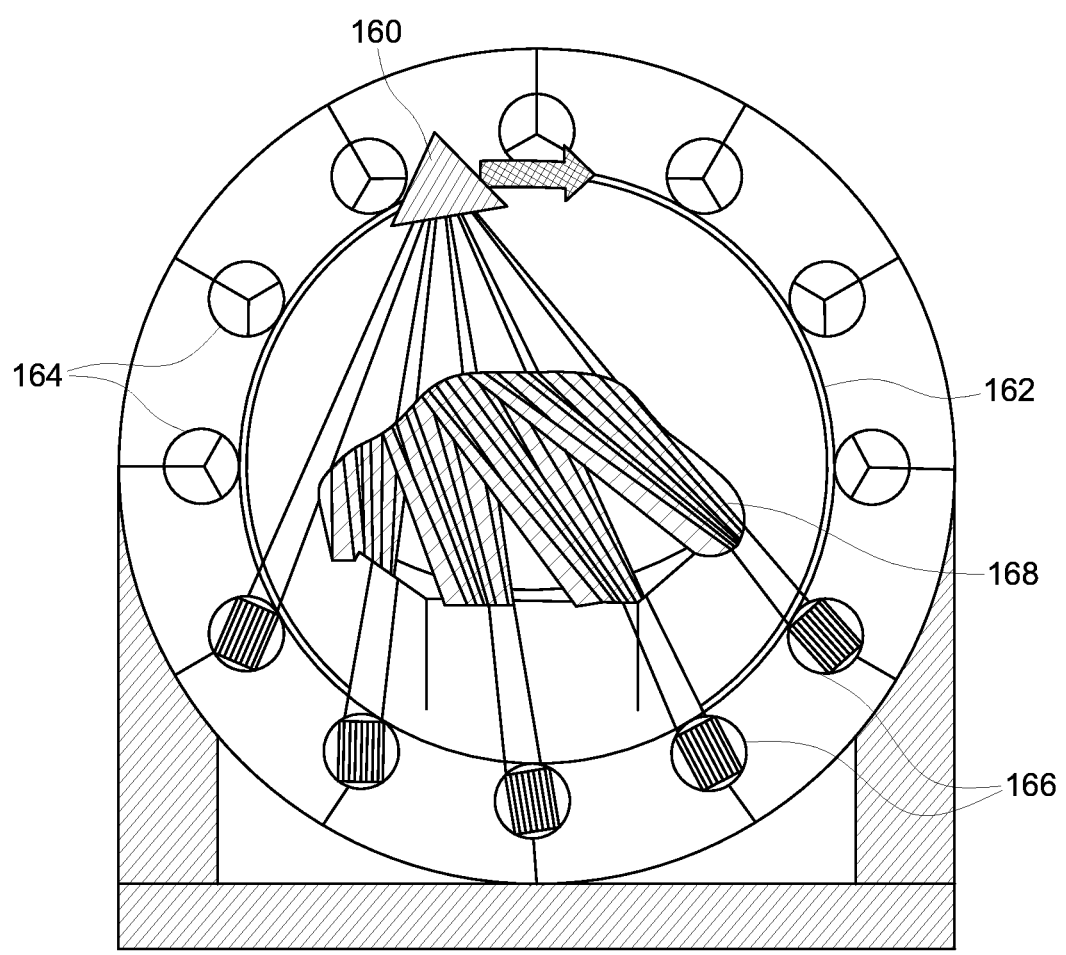
FIG. 13 shows a seventh movement location of an x-ray tube during an x-ray data scan, according to an embodiment.

FIG. 13 shows a seventh movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 13 shows five angles α of transmission to five active detectors 166. Another detector on the lower left has become an active detector 166.

Figure 14:
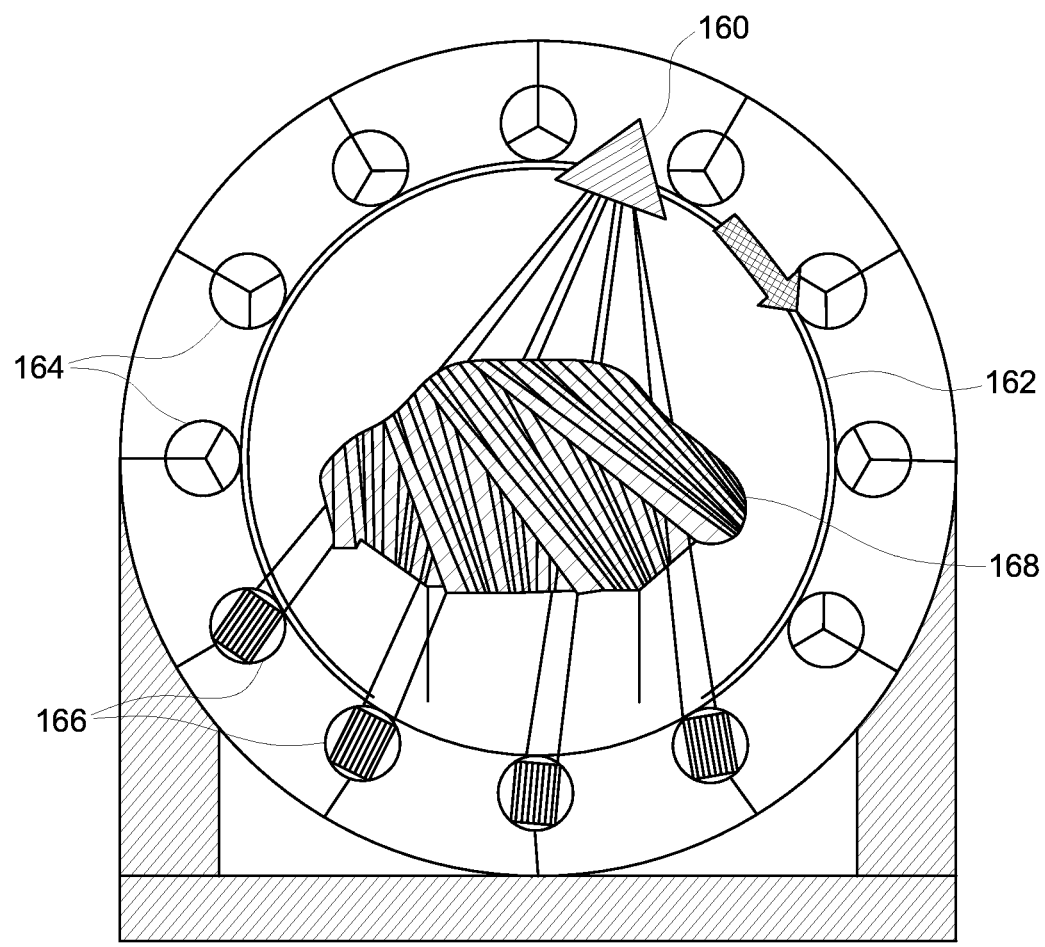
FIG. 14 shows a final movement location of an x-ray tube during an x-ray data scan, according to an embodiment.

FIG. 14 shows a final movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 14 shows four angles α of transmission to four active detectors 166. Another detector on the lower right has become an inactive detector 164. Subject 168 has had almost all areas of the X-Y cross section in the bore scanned with the x-ray tube not completing a full revolution around the circumference of the bore. A quick scan such as shown can give low quality data to assist with simultaneous or future emission (such as PET or SPECT or NM) imaging. It should be noted that FIG. 14 shows that the detector heads have continued to be angled towards x-ray tube 160 as it has moved around the circumference of the bore. For applications such as attenuation correction, 180 degrees or 360 degrees single revolution of x-ray tube 160 may be enough. Thus, an adequate CT image can be made from the x-ray scan data, even when 20% total angle α coverage. In other applications, the system may run a helical scan by including movement of the table as part of the x-ray scan data. The height of the bed/pallet may also be adjusted to improve image quality. Additional ways to improve the x-ray scan coverage and CT image results are discussed herein.

Figure 15:
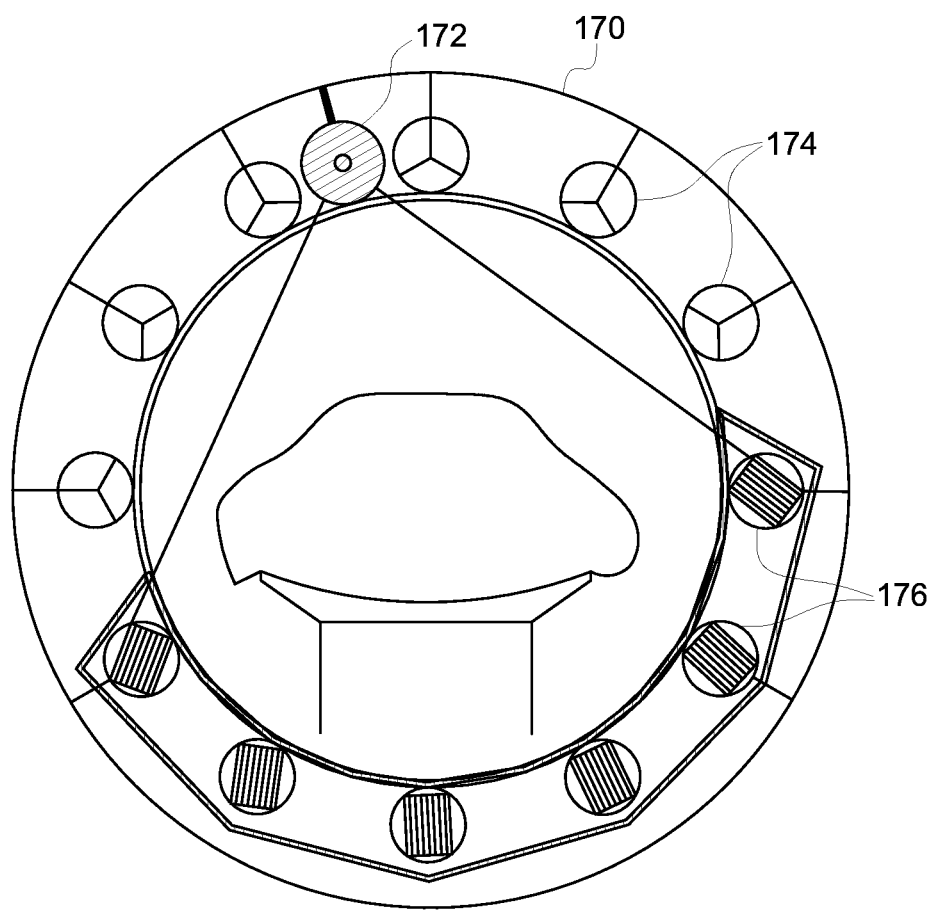
FIG. 15 shows an imaging system with a single rotary member attached to a gantry, according to an embodiment.

FIG. 15 shows an imaging system with a single rotary member 170 attached to a gantry, according to an embodiment. X-ray tube 172, emission detectors 174, and dual detectors 176 are all attached to rotary member 170. X-ray tube 172 is attached to rotary member 170 between the installations of two emission detectors 174. Thus, only a portion of the image detectors in the system, dual detectors 176, need to be able to handle x-ray transmission data. FIG. 15 shows six dual detectors 176 and six emission detectors 174, according to an embodiment. Thus, the system can include emission-only detectors. These can be preferred in some embodiments as they can be less expensive or faster in image transmission. Rotary member 170 rotates orbitally around a subject and moves X-ray tube 172, emission detectors 174, and dual detectors 176 along with it to perform x-ray scan imaging. Dual detectors 176 always have the same detector head angle towards x-ray tube 172 in this embodiment. Sweep motors thus may be not needed for dual detectors 176 then in this case, saving cost and complexity. This embodiment can be less expensive, lighter, and simpler to produce and maintain. Alternatively, a detector column can be removed from the system and the x-ray tube placed in its location. This is helpful in circumstances where the x-ray tube is large.

Figure 16:
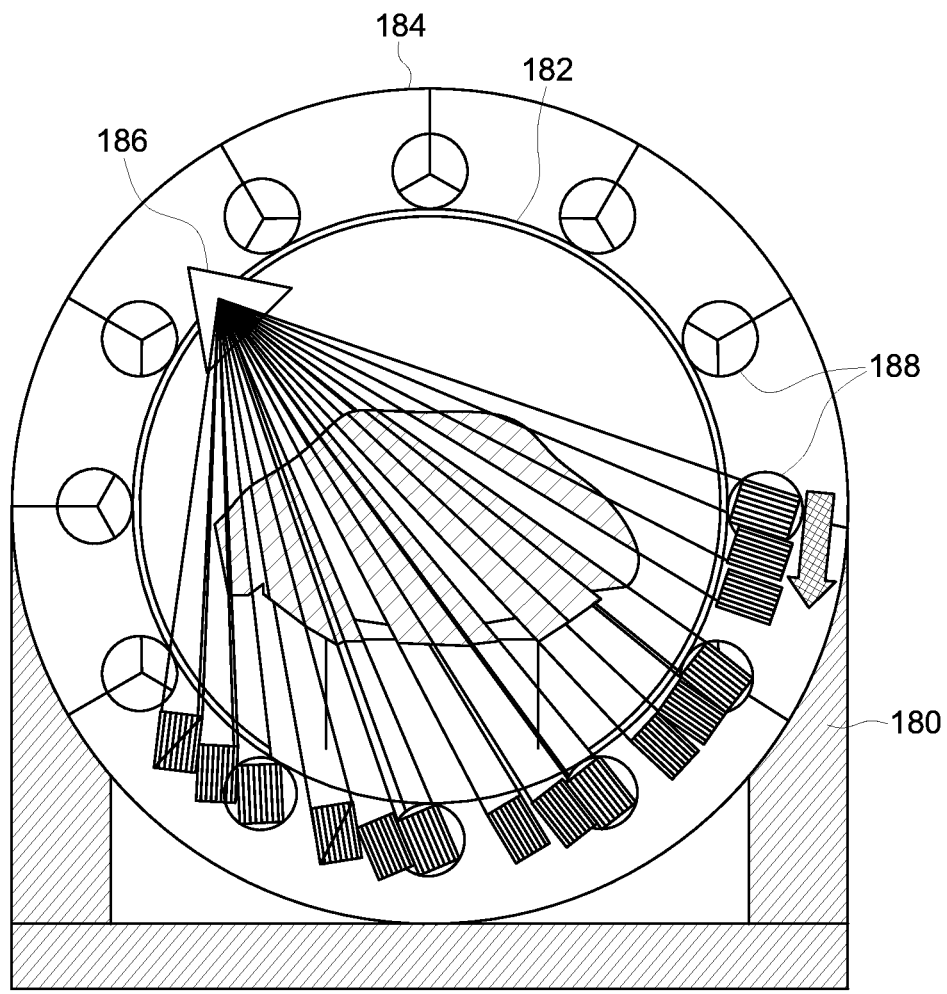
FIG. 16 shows an imaging system with image detectors attached to a rotary member, according to an embodiment.

FIG. 16 shows an imaging system with image detectors 188 attached to a rotary member 184, according to an embodiment. Rotary member 184 may perform a 360 degree or less rotation. X-ray tube 186 is attached to stationary structure 182, which is part of gantry 180. In this embodiment, x-ray tube 186 is stationary and the image detectors 188 are rotated orbitally around the circumference of the bore by rotary member 184. FIG. 16 shows the detector head angles adjusting to be pointing towards x-ray tube 186 as the image detectors 188 revolve around the gantry.

Figure 17:
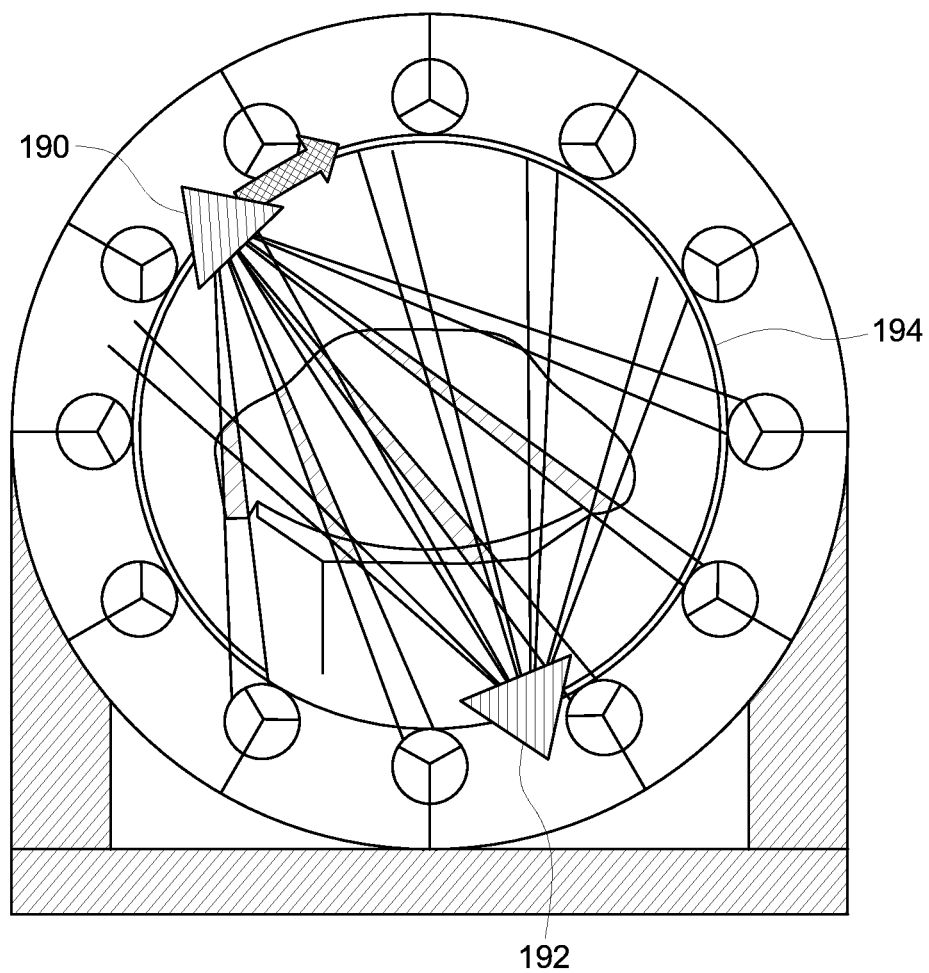
FIG. 17 shows an imaging system with multiple x-ray tubes, according to an embodiment.

FIG. 17 shows an imaging system with multiple x-ray tubes, according to an embodiment. First x-ray tube 190 and second x-ray tube 192 are attached to rotary member 194. Image detectors in the system detect the x-ray data to reconstruct CT images and correct/enhance NM images. The x-ray tubes may be set at the same or varying power levels. The x-ray tubes may be set at similar or varying offsets. These alterations allow the detectors to pick up different x-ray scan data sets for best image quality results. The x-ray tubes may be used simultaneously or in sequence. While not shown, more than two x-ray tubes may be included in the system. In an embodiment, each detector column has an integrated x-ray tube for transmitting x-rays. In an embodiment, an x-ray tube is placed in each gap between detector columns. In an embodiment, an x-ray tube with a non-rotating anode may be used. In an embodiment, an x-ray tube with multiple focal spots may be used for electronically shifting the x-ray source location.

Figure 18:
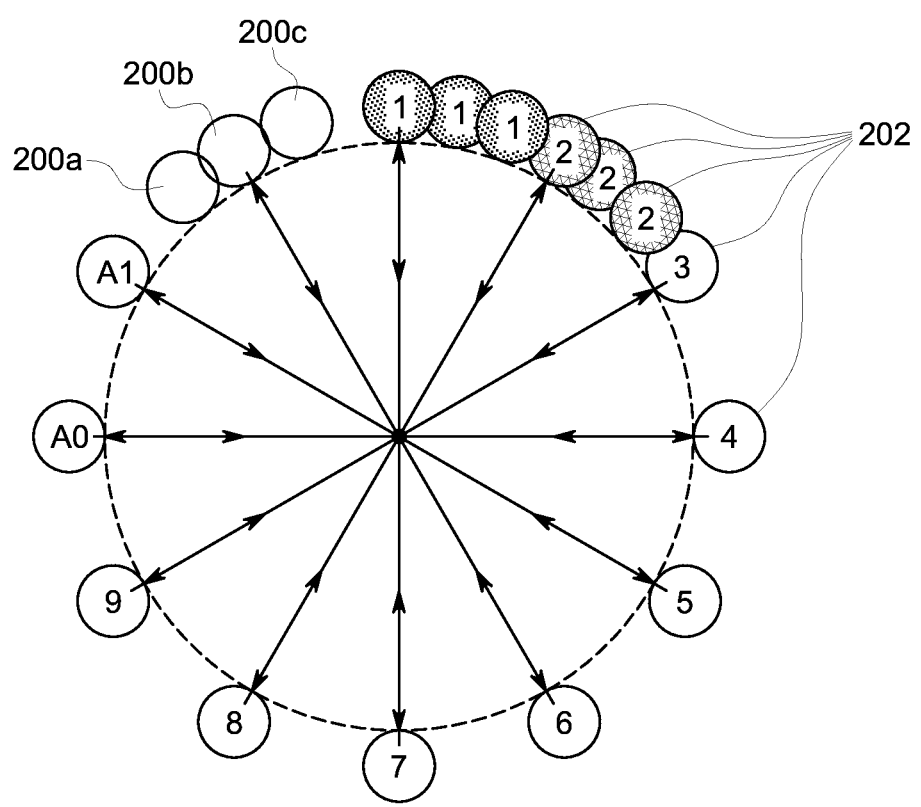
FIG. 18 shows an imaging system where an x-ray tube and image detectors do not rotate, according to an embodiment.

FIG. 18 shows an imaging system where an x-ray tube, in locations 200a, 200b, 200c, and image detectors 202 do not rotate, according to an embodiment. Thus, the system is made simpler and has less chance of rotation maintenance issues. Instead, the x-ray tube and image detectors 202 have multiple steps. Thus, each item in the system has three, for example, step locations. A left, right, and middle, for example. The system has many configurations for scanning and detecting data without having a rotary member. By adjusting the x-ray tube to positions 200a, 200b, and 200c, the system increases the x-ray scan coverage. This multiple step feature can be included in any of the previous embodiments to increase scan data coverage. FIG. 18 also shows an imaging system where the x-ray tube may be retracted or extended towards a subject, according to an embodiment. The patient bed or pallet can have steps as well to position the patient at different location in the X-Y plane, e.g. higher, lower, right, or left. This also provides additional coverage for image detection.

In an embodiment, the system can have one rotary member and one step member. For example, the x-ray tube can be attached to the rotary member for full orbit around a patient. The detector columns can be attached to the step member that only steps into one to three new positions.

Figure 19:
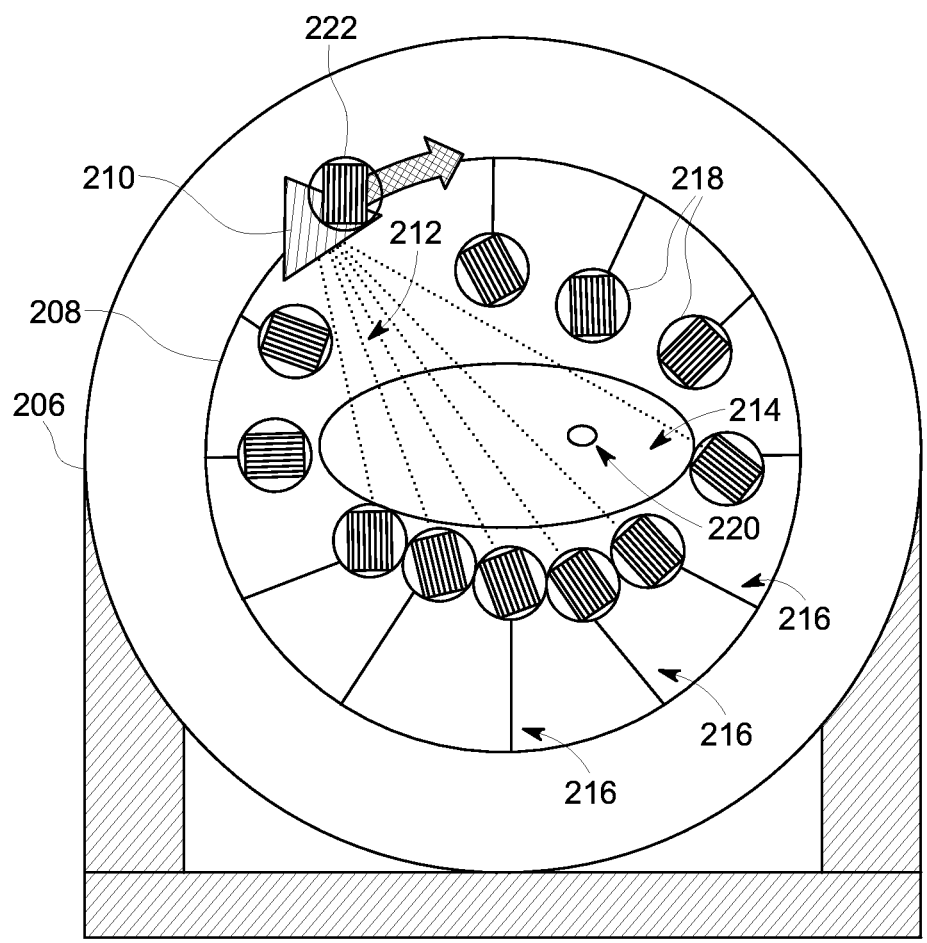
FIG. 19 shows a medical imaging system performing a concurrent NM and CT scan, according to an embodiment.

FIG. 19 shows a medical imaging system performing a concurrent NM and CT scan, according to an embodiment. X-ray tube 210 is attached to rotary member 208. X-ray tube 210 emits x-rays 212 through patient 214 towards dual x-ray/emission active detectors 216. Active image detectors 216, inactive emission detectors 218, and blocked detector 218 can be attached to rotary member 208 or stationary structure 206. Active image detectors 216 have been radially moved towards patient 214 and have their detector heads pointing towards x-ray tube 210. Inactive image detectors 218 have been radially moved towards patient and have their detector heads pointing towards patient ROI 220. Inactive image detectors 218 may also point not just directly to ROI 220, but to define an angular scanning range for small sweeps across the entire ROI 220 distance or width. Blocked detector 218 is retracted to allow pass-by of x-ray tube 210 and may be set into use after x-ray tube 210 has passed.

The system benefits from only needing one orbit of detectors for both CT transmissions and NM/PET emissions. This saves cost and room space from needing to have two sets of detectors. Improvements to the NM/PET image due to attenuation, body shape, ROI determination and other uses of CT data help the system be efficient and provide the best image quality output for users, which may be doctors in an embodiment.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
a gantry having a bore extending therethrough;
a plurality of image detectors attached to the gantry and radially spaced apart along a circumference of the bore at one or more predetermined intervals such that gaps exist between image detectors along the circumference of the bore; and
an x-ray source attached to the gantry, wherein the x-ray source transmits x-rays across the bore towards at least two of the image detectors;
wherein at least one image detector detects both emission radiation and x-ray radiation.

2. The imaging system of claim 1, the gantry further comprising:
a stationary structure and a rotary member;
wherein the x-ray source is attached to the rotary member and the plurality of image detectors are attached to the stationary structure; and
wherein the rotary member rotates to allow the x-ray source to orbit an imaging subject inside the bore.

3. The imaging system of claim 2, each image detector further comprising:
a sweep motor;
a detector head comprising detector elements; and
wherein, if the image detector is in an x-ray transmission fan beam, the sweep motor adjusts the angle of the detector head to be directed at the x-ray source.

4. The imaging system of claim 3, each image detector further comprising:
a radial motor for extending the image detector closer to and retracting the image further from a region of interest; and
wherein, if the image detector is not in the x-ray transmission fan beam, the sweep motor adjusts an angle of the detector head to be directed at the region of interest and the radial motion motor extends or retracts the image detector based on its distance to the region of interest.

5. The imaging system of claim 1, the gantry further comprising:
a stationary structure and a rotary member;
wherein the plurality of image detectors are attached to the rotary member and the x-ray source is attached to the stationary structure; and
wherein the rotary member rotates to allow the imaging detectors to orbit an imaging subject inside the bore.

6. The imaging system of claim 1, the gantry further comprising:
a first rotary member and a second rotary member, wherein both rotary members are annular; and
wherein the plurality of image detectors are attached to the first rotary member and the x-ray source is attached to the second rotary member.

7. The imaging system of claim 6, wherein:
the plurality of detectors rotate around the bore on an outer circumference; and
the x-ray source rotates around the bore on an inner circumference.

8. The imaging system of claim 1, wherein:
the transmitted x-rays are transmitted in a fan beam; and
more than fifty percent of the fan beam angle is gap transmission in that x-rays enter the gaps and do not hit an image detector.

9. The imaging system of claim 8, the x-ray source further comprising:
a collimator; and
wherein a processor in the system directs the collimator to block gap transmissions.

10. The imaging system of claim 1, further comprising an image reconstruction module that:
receives emission radiation and x-ray radiation from the plurality of image detectors and
generates medical images; and
outputs the medical images to a display or a memory device.

11. The imaging system of claim 10, wherein:
the image reconstruction module uses the emission radiation to reconstruct a first medical image and uses the x-ray radiation to perform attenuation correction on the first medical image to generate a second medical image.

12. The imaging system of claim 10, wherein:
each image detector further comprises:
a sweep motor;
a detector head comprising detector elements;
a radial motor for extending and retracting the image detector;
the image reconstruction module uses the x-ray radiation to determine the location of a region of interest;
the radial motor extends the image detector towards the region of interest;
the sweep motor adjusts the detector head angle to be directed towards the region of interest; and
the detector elements detect emission radiation.

13. The imaging system of claim 10, wherein:
the image reconstruction module uses the emission radiation to reconstruct a second medical image and uses the x-ray radiation to determine an anatomical shape related to the second medical image.

14. The imaging system of claim 1, wherein:
the x-ray source transmits low-power x-rays.

15. The imaging system of claim 1, wherein:
the image detectors are regularly spaced around the circumference of the bore such that the gaps between image detectors are substantially equivalent.

16. The imaging system of claim 1, wherein:
the image detectors are irregularly spaced around the circumference of the bore such that the gaps between image detectors are not equivalent.

17. The imaging system of claim 1, the image detectors further comprising:
detector elements made from Cadmium Zinc Telluride (CZT).

18. The imaging system of claim 1, further comprising:
a second x-ray source attached to the gantry.

19. The imaging system of claim 1, wherein:
the plurality of image detectors is eleven image detectors or twelve image detectors.

20. The imaging system of claim 1, wherein:
the system activates the image detectors that are in a x-ray transmission fan beam and does not activate the image detectors that are outside of the x-ray transmission fan beam.

21. The imaging system of claim 1, wherein:
the image detectors are photon counting detectors.

22. The imaging system of claim 1, wherein:
the emission radiation is single photon emission computed tomography (SPECT) radiation.

23. The imaging system of claim 1, wherein:
the x-ray source and the plurality of image detectors share an X-Y plane.

24. An imaging method, comprising:
rotating an x-ray source around the circumference of a gantry bore;
receiving transmitted x-ray radiation at a plurality of image detectors spaced evenly apart along the circumference of the bore at a predetermined interval such that gaps exist between image detectors along the circumference of the bore;
receiving emission radiation at a plurality of the plurality of image detectors; and
generating a medical image based on the emission radiation and x-ray radiation.

25. The imaging method of claim 24, wherein:
the emission data is used to generate an intermediate image; and
the x-ray data is used to perform attenuation correction on the intermediate image to generate the medical image.

26. The imaging method of claim 24, further comprising:
determining a region of interested based on the x-ray radiation; and
adjusting the angular scanning range of at least two detector heads to be directed towards the region of interest.

* * * * *